(12) United States Patent
Carrubba

(10) Patent No.: US 8,657,799 B2
(45) Date of Patent: Feb. 25, 2014

(54) OSTOMY APPLIANCE AND METHOD

(76) Inventor: Georgann M. Carrubba, Batavia, NY (US)

( * ) Notice: Subject to any disclaimer, the term of this patent is extended or adjusted under 35 U.S.C. 154(b) by 0 days.

(21) Appl. No.: 13/290,290

(22) Filed: Nov. 7, 2011

(65) Prior Publication Data
US 2013/0116636 A1 May 9, 2013

(51) Int. Cl.
A61M 1/00 (2006.01)

(52) U.S. Cl.
USPC .......................................................... 604/318

(58) Field of Classification Search
USPC .......................................................... 604/318
See application file for complete search history.

(56) References Cited

U.S. PATENT DOCUMENTS

| 2,639,710 | A | * | 5/1953 | Fazio | 604/342 |
| 2,708,802 | A | * | 5/1955 | Baker et al. | 40/331 |
| 3,690,320 | A | | 9/1972 | Riely | |
| 3,736,934 | A | * | 6/1973 | Hennessy | 604/342 |
| 3,825,005 | A | | 7/1974 | Fenton | |
| 4,219,023 | A | | 8/1980 | Galindo | |
| 4,294,252 | A | * | 10/1981 | Einset | 604/345 |
| 4,439,191 | A | | 3/1984 | Hogan | |
| 4,460,363 | A | * | 7/1984 | Steer et al. | 604/336 |
| 4,519,797 | A | | 5/1985 | Hall | |
| 4,543,097 | A | | 9/1985 | Van Polen | |
| 4,723,951 | A | * | 2/1988 | Steer | 604/333 |
| 4,784,656 | A | * | 11/1988 | Christian | 604/355 |
| 4,846,798 | A | * | 7/1989 | Holtermann et al. | 604/339 |
| 4,950,223 | A | | 8/1990 | Silvanov | |
| 5,098,420 | A | * | 3/1992 | Iacone | 604/338 |
| 5,178,615 | A | * | 1/1993 | Steer et al. | 604/338 |
| 5,209,744 | A | * | 5/1993 | Abe et al. | 604/342 |
| 5,248,308 | A | | 9/1993 | von Emster | |
| 5,312,381 | A | | 5/1994 | Brooks | |
| 5,470,325 | A | * | 11/1995 | Fundock | 604/332 |
| 5,520,670 | A | * | 5/1996 | Blum | 604/338 |
| 5,617,616 | A | * | 4/1997 | Cutts, Sr. | 24/30.5 R |
| 5,626,569 | A | | 5/1997 | Holtermann et al. | |
| 5,759,180 | A | | 6/1998 | Myhres | |
| 5,785,695 | A | * | 7/1998 | Sato et al. | 604/339 |
| 5,843,054 | A | | 12/1998 | Honig | |
| 5,968,024 | A | * | 10/1999 | Freeman | 604/334 |
| 6,050,982 | A | * | 4/2000 | Wheeler | 604/332 |
| D452,374 | S | | 12/2001 | Kim | |
| 6,415,947 | B1 | | 7/2002 | Kim | |
| 6,679,866 | B1 | * | 1/2004 | Gunawan | 604/338 |
| D488,031 | S | | 4/2004 | Kim | |

(Continued)

FOREIGN PATENT DOCUMENTS

CN 201840569 5/2011
DK 177034 B1 2/2011

(Continued)

Primary Examiner — Susan Su
Assistant Examiner — Guy K Townsend
(74) Attorney, Agent, or Firm — Woods Oviatt Gilman LLP; Katherine M. McGuire, Esq.

(57) ABSTRACT

An ostomy appliance includes a translucent receptacle for releasably securing to the stoma flange with the gathered ostomy pouch located within the receptacle. No or negligible pressures are applied to the stoma which remains clear and healthy. The user may use the receptacle during times of physical or personal activity when additional discreteness is desired. The pouch may be made of a material having a thermochromatic ink which changes color with heat such that the user may visually inspect and identify when waste is present in the pouch.

7 Claims, 3 Drawing Sheets

(56) References Cited

U.S. PATENT DOCUMENTS

| | | | |
|---|---|---|---|
| 6,764,473 B2 * | 7/2004 | Morton | 604/334 |
| 6,793,096 B1 | 9/2004 | Seok | |
| D499,931 S | 12/2004 | Kim | |
| 7,722,586 B2 | 5/2010 | Mullejans et al. | |
| 7,857,796 B2 * | 12/2010 | Cline et al. | 604/338 |
| 7,931,631 B2 * | 4/2011 | Pedersen et al. | 604/344 |
| 2005/0113770 A1 * | 5/2005 | Pedersen et al. | 604/332 |
| 2005/0256466 A1 * | 11/2005 | Winkler | 604/337 |
| 2006/0258997 A1 | 11/2006 | Belt | |
| 2008/0294129 A1 | 11/2008 | Giori et al. | |
| 2009/0234312 A1 * | 9/2009 | O'Toole et al. | 604/332 |

FOREIGN PATENT DOCUMENTS

| | | |
|---|---|---|
| EP | 1 348 411 A1 | 1/2003 |
| EP | 1 985 267 A1 | 10/2008 |
| KR | 10-0983870 | 9/2010 |
| WO | WO 2011/031822 A1 | 3/2011 |

* cited by examiner

OSTOMY APPLIANCE AND METHOD

BACKGROUND OF THE INVENTION

The present invention relates to ostomy appliances. More particularly, the present invention relates to an ostomy appliance which is designed to provide a high level of discreteness to the user on an as needed basis.

An "ostomy" is the generic term for a surgical procedure such as the ileostomy, colostomy and urostomy which leave the patient with a digestive waste opening formed by attaching the patient's intestine (small intestine in the case of an ileostomy; large intestine in the case of a colostomy) to the perimeter of an incision made in the abdominal wall. This part of the intestine is surgically opened to form what is called the "stoma" wherethrough digestive waste exits the body. The procedure may be reversible or irreversible depending on the circumstances. It is estimated that up to 750,000 Americans have an ostomy.

A digestive waste collection pouch is attached about the stoma to collect the waste existing therefrom. The collection pouch and associated body attachment parts are commonly referred to as the ostomy appliance or assembly. Ostomy appliances are offered in single piece and two piece systems. In the single piece system, the pouch has an opening which is aligned with an opening in and then permanently fixed to a disc or flange which has an adhesive surface opposite the pouch which secures the flange and pouch to the body about the stoma. In the two-piece system, the pouch is detachably secured to the flange, commonly via a snap ring on the flange which fits into a cooperatively formed groove attached to the perimeter of the pouch opening. In either the single or two piece systems, the pouch typically includes an open end opposite the flange end which may be alternately open and closed using a clamp. The bag is clamped closed during use and opened to empty the waste contents from the bag. The bag may be cleaned and reused or discarded with a new bag being attached to the flange.

Users of ostomy appliances often complain about the inconveniences of the appliance including lack of discreteness. For example, there is no control over when waste deposits into the bag which may thus fill and noticeably expand beneath the clothing at inconvenient times, inevitably causing embarrassment to the user. Attempts to address this problem have been at best a minor improvement while others appear to pose the threat of actual physical harm to the user by applying a positive pressure against the stoma.

There therefore exists a need for an improved ostomy appliance and method which provides the user the option of temporarily containing the ostomy pouch in a small container held close to the body in a manner which provides enhanced discreteness during periods of physical activity and close personal encounters without application of potentially dangerous pressures on the stoma as occurs in the prior art.

SUMMARY OF THE INVENTION

The present invention successfully addresses the drawbacks of the prior art by providing an ostomy appliance and method which includes a cup-shaped receptacle having an attachment mechanism about the open perimeter thereof which may be releasably secured to a mating attachment mechanism secured to the perimeter of the stoma opening of the ostomy appliance flange. When it is desired to contain the pouch for increased discreteness, the user simply gathers or rolls the pouch up upon itself, positions the receptacle over the pouch and then secures the cooperative attachment mechanisms together thereby securing the receptacle to the ostomy flange with the pouch enclosed therein in a loosely gathered or rolled condition. The receptacle may have one or more vent holes formed therein to allow gas to escape therefrom. A fabric cover may be placed over the receptacle to provide further discreteness and comfort to the user.

When the pouch is held in the receptacle, waste will deposit therein in the usual manner. As waste enters the pouch, the pouch will begin to expand within the confines of the receptacle. There is thus no positive pressure being applied to the stoma and waste is allowed to naturally exit the stoma and enter the pouch. It is not intended that the receptacle be in place over the pouch for more than a few hours at a time and it is therefore not expected that waste will be prevented from naturally exiting the stoma for any potentially harmful extended period of time. Rather, the receptacle is only intended to be in place during times when the user would like an increased level of discreteness and control over evacuation into the pouch. Once the pouch is full and/or the receptacle is no longer needed, the user simply detaches the receptacle from the flange whereupon the pouch is allowed to fully expand and left attached to the flange to completely fill or removed/cleaned as desired.

In another embodiment of the invention, the pouch is constructed such that it changes color with the application of heat. In this way, the user may quickly check to see if there is waste in the pouch. Since the receptacle may be made of translucent plastic, the user need not remove the receptacle in order to check the status of the pouch.

DETAILED DESCRIPTION OF A PREFERRED EMBODIMENT

Figure 1:
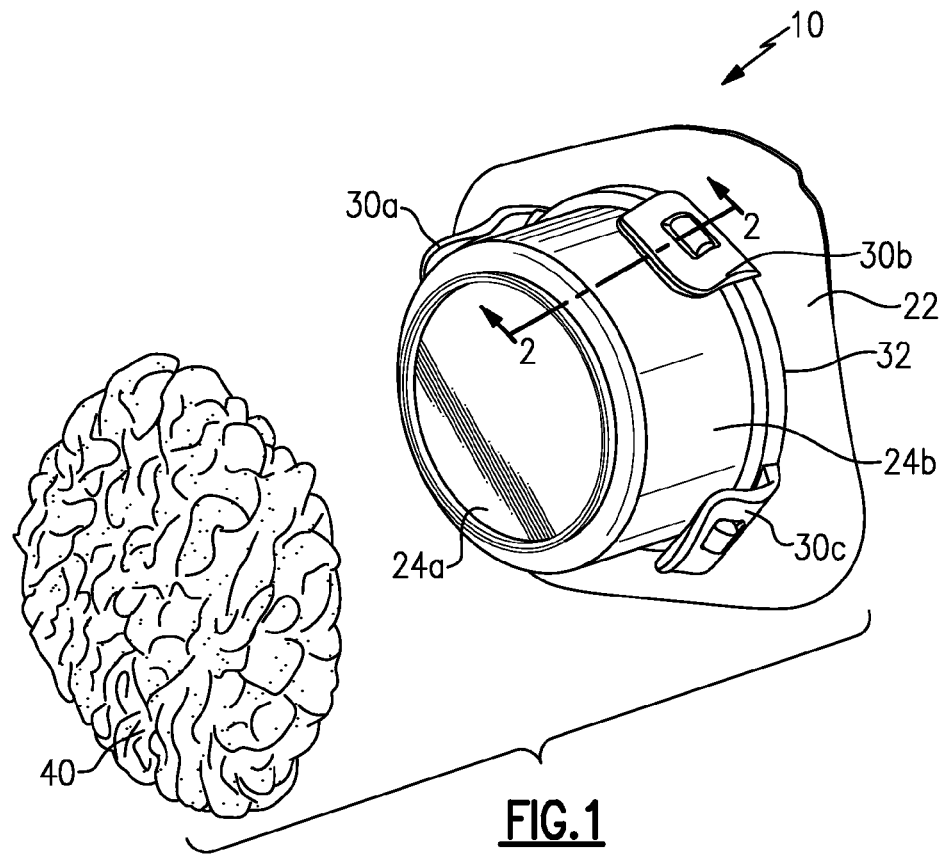
FIG. 1 is a perspective view of an embodiment of the inventive ostomy device.

Referring now to the drawing, there is seen in the various figures an ostomy appliance according to one embodiment of the invention indicated generally by the reference numeral 10. Ostomy appliance 10 includes a disc 12 having a central opening 14 for aligning with and positioning over a user's stoma (not shown). Disc 12 includes an adhesive surface 12*a* (see FIG. 2) for securing disc 12 to the stoma body tissue. Release paper (not shown) protects the adhesive surface 12*a* until time of use whereupon the user removes the release paper and adhesively secures the disc surface 12*a* onto the stoma tissue with the opening of the stoma aligned with the disc opening 14.

Disc 12 is attached to a ring-shaped flange 16 which may be releasably secured to a cooperatively sized ring-shaped groove 18 attached to the perimeter of a first opening 20*a* of waste collection pouch 20. Of course the groove and flange may be interchanged (i.e., the groove 18 may be located on the disc 12 and the flange may be located on the pouch 20), and other releasable attachment mechanisms may be used in place of the groove and flange. A skirt 22 is fixedly secured to (e.g., by heat welding) and extends outwardly from ring-shaped flange 16. Skirt 22 includes an adhesive surface 22a for adhering to the user's body tissue which surrounds the stoma. A release paper (not shown) may protect the adhesive surface 22a until time of use whereupon the user removes the release paper and adhesively secures the skirt 22 to the user's body while also adhering the disc adhesive surface 12a to the adjacent stoma tissue as described above.

Figure 6:
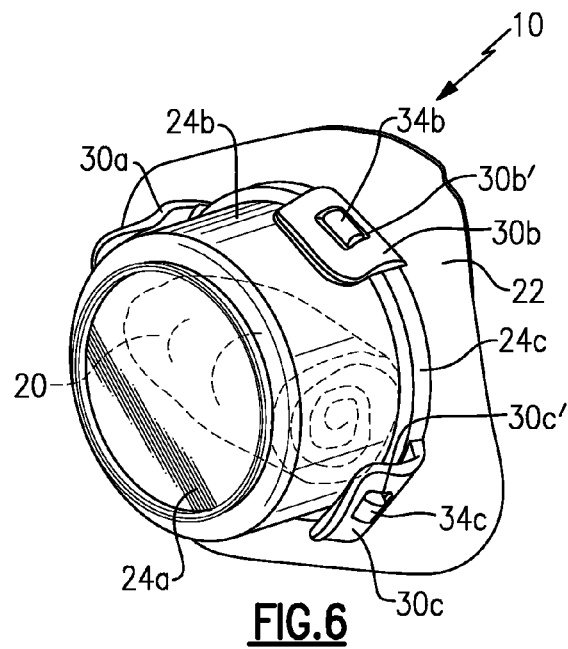
FIG. 6 is the view of FIG. 5 showing the ostomy bag container attached to the stoma flange with the folded bag showing in dotted lines inside the container.
Figure 5:
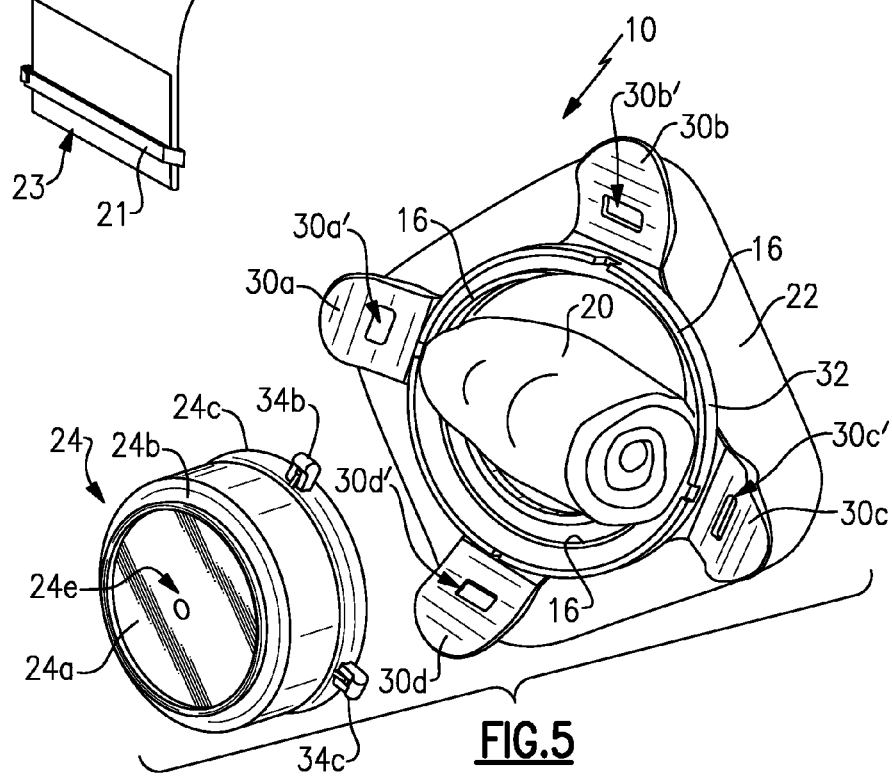
FIG. 5 is the view of FIG. 4 showing the ostomy bag in the folded condition and the ostomy bag container in spaced relation thereto.

A cup-shaped receptacle 24, which may be made of a translucent plastic, is provided for times when the user desires an increased level of discreteness. Receptacle 24 includes a bottom wall 24a and a side wall 24b terminating in a top perimeter edge 24c all defining an interior cavity 24d. As seen in FIG. 5, receptacle bottom wall 24a may include a small aperture 24e to allow gases to vent therethrough. A receptacle attachment mechanism is provided for releasably securing receptacle 24 to the disc 12/flange 22 combination. The receptacle attachment mechanism may take the form of one or more but preferably four hinged tabs 30a-d extending from a ring-shaped base 32 which encircles flange 16, and an equal number of alignable projections 34a-d extending from receptacle 24 adjacent perimeter edge 24c. Each tab 30a-d includes a respective opening 30a'-d' wherethrough a like number of respectively aligned projections 34a-d may pass and releasably engage to a respective tab via a snap (interference) fit and thereby releasably securing receptacle 24 to ring 32. The top perimeter edge 24c of receptacle 24 may fit inside a groove 36 provided in base 32 to further seal the receptacle 24 to the base 32. Prior to securing receptacle 24 to ring 32, the user either loosely gathers or rolls pouch 20 up upon itself as shown in FIG. 5. Once receptacle 24 is attached to ring 32 in the manner described, pouch 20 is located within receptacle 24 either loosely gathered or rolled as shown in FIG. 6. Although mating tabs and projections are described and shown herein as comprising the receptacle attachment mechanism, it is of course understood that other known attachment mechanisms which may releasably secure receptacle 24 to ring 32 may be used as desired.

Figure 2:
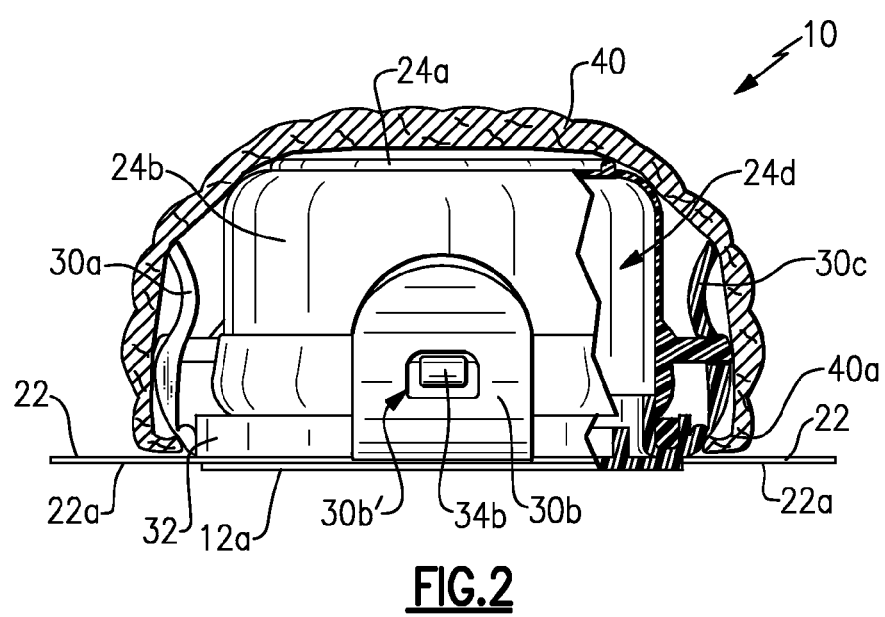
FIG. 2 is a side elevational view of the ostomy device of FIG. 1 showing the covering in position over the ostomy bag container with parts thereof shown in section.
Figure 3:
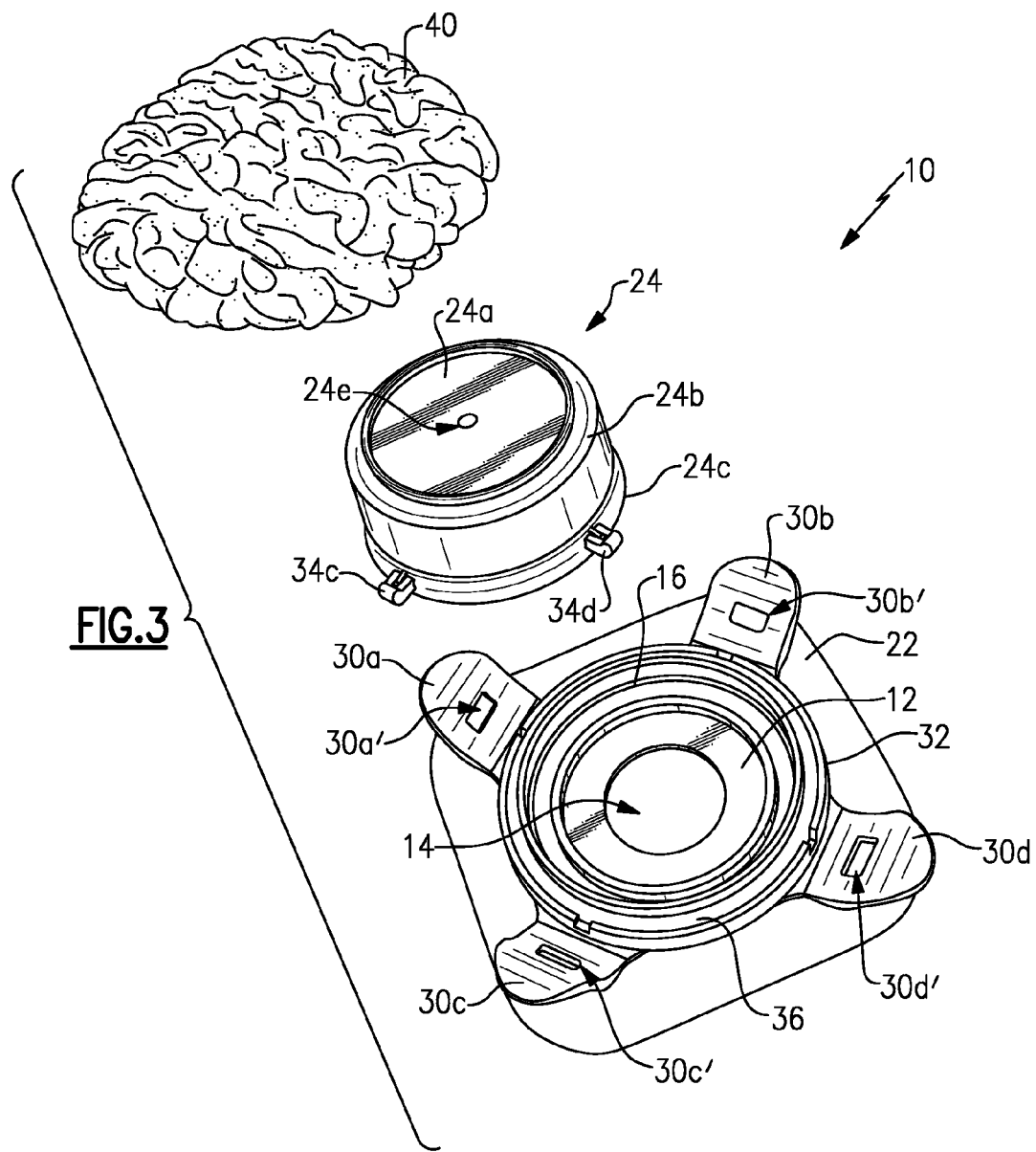
FIG. 3 is an exploded perspective view of the ostomy device absent the ostomy bag.

As described above, waste is free to enter pouch 20 which may expand up to the confines of receptacle 24. Since the pouch is only loosely gathered (and if rolled, it is not rolled tightly), there is no positive pressure (or at most only a negligible amount) applied to the stoma during this time. The stoma is thus free of any potentially harmful effects caused by positive pressures applied thereto as seen in some prior art ostomy appliances. The user may cover receptacle 24 with a fabric covering 40 having an elasticized opening 40a as seen in FIG. 2. In this manner, the user has increased his/her level of discreteness by confining their ostomy pouch 20 to a relatively small receptacle 24 with a soft fabric covering 40. The user may thus engage in physical or other social activities with a greater sense of discreteness due to the control and concealment of the ostomy pouch afforded by receptacle 24.

Figure 4:
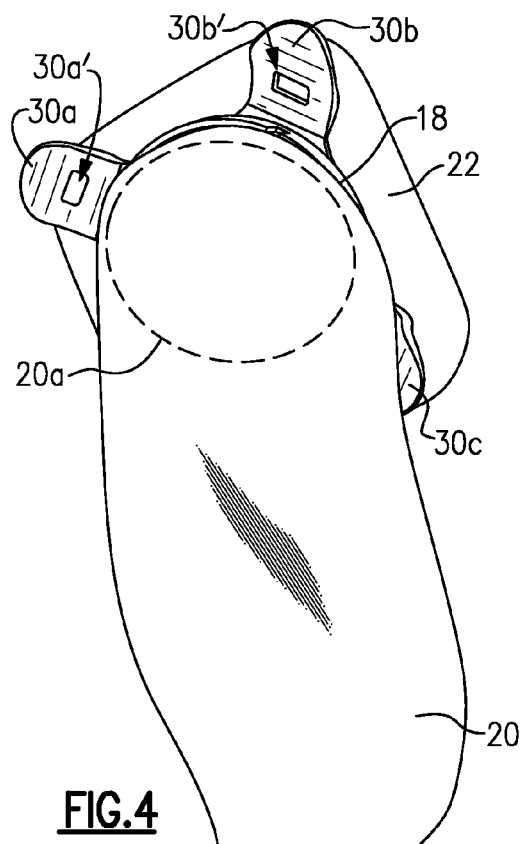
FIG. 4 is a perspective view showing the ostomy bag attached to the stoma flange with the bag in the unfolded position.

Other embodiments of the invention may include features such as making pouch 20 and/or receptacle 24 of a color changing material which is activated with increased heat. When waste is depositing into the pouch, the heat of the waste will heat the pouch and/or receptacle which in turn will change color, alerting the user that it may be time to check their ostomy pouch for possible emptying or changing. Emptying the pouch for re-use and without removal from the skirt 22 is accomplished by releasing clamp 21 to unseal second pouch opening 23 located at the end opposite first opening 20a (see FIG. 4). Such color changing materials are known and may comprise, for example, thermochromatic inks such as seen in U.S. Pat. Nos. 5,223,958, 5,219,625, 6,759,099, 6,902,775, 6,281,165 and U.S. Published Patent Application No. US20060228498, for example, the entireties of which are incorporated herein by reference.

While the invention has been shown and described with reference to particular embodiments thereof, it is understood that functionally equivalent variations may be made thereto without departing from the full spirit and scope of the invention as defined by the claims which follow.

What is claimed is:

1. An ostomy appliance, comprising:
    a) a disc having an adhesive surface for applying to stoma tissue;
    b) a ring-shaped flange attached to said disc on the surface thereof opposite said adhesive surface;
    c) a pouch having a first opening having a ring-shaped groove attached to the perimeter of said first opening, said ring-shaped groove releasably attachable to said ring-shaped flange to releasably attach said pouch to said disc;
    d) a receptacle having a bottom wall, side wall and top perimeter edge defining an interior cavity;
    e) a receptacle releasable attachment mechanism adapted to releasably secure said receptacle to said ring-shaped flange with said pouch gathered and located within said receptacle.

2. The ostomy appliance of claim 1 wherein said releasable attachment mechanism comprises one or more hinged tabs each having an opening and extending from a base positioned about said ring-shaped flange, and a like number of projections extending from said receptacle side wall which may be respectively aligned with said tabs whereby said projections are passed through a respective tab opening to thereby releasably engage said tabs to a respective said projection via an interference fit.

3. The ostomy appliance of claim 1 wherein said pouch includes a color changing material which is activated by heat.

4. The ostomy appliance of claim 1, and further comprising a fabric cover adapted to be removably positioned in covering relation over said receptacle.

5. The ostomy appliance of claim 1, wherein said receptacle is made of a translucent material.

6. The ostomy appliance of claim 1 and further comprising a pouch clamp, and wherein said pouch includes a second opening opposite said first opening, said second opening adapted to be selectively sealed closed with said pouch clamp and selectively opened via removal of said pouch clamp.

7. An ostomy appliance, comprising:
    a) a disc having an adhesive surface for applying to stoma tissue;
    b) a ring-shaped flange attached to said disc on the surface thereof opposite said adhesive surface;
    c) a pouch having a first opening having a ring-shaped groove attached to the perimeter of said first opening, said ring-shaped groove releasably attachable to said ring-shaped flange to releasably attach said pouch to said disc, said pouch including a color changing material which is activated by heat enabling a user to identify when waste is collected in said pouch;
    d) a translucent receptacle having a bottom wall, side wall and open top perimeter edge defining an interior cavity;
    e) a receptacle releasable attachment mechanism adapted to releasably secure said receptacle to said ring-shaped flange with said pouch gathered and located within said receptacle, wherein said releasable attachment mechanism comprises one or more hinged tabs extending from a base with each said tab having an opening, and a like number of projections extending from said receptacle side wall which may be respectively aligned with said tabs whereby said projections are passed through a respective tab opening to thereby releasably engage said tabs to a respective said projection via an interference fit.

\* \* \* \* \*